(12) United States Patent
Roell et al.

(10) Patent No.: US 10,253,290 B2
(45) Date of Patent: Apr. 9, 2019

(54) BIOREACTOR ARRANGEMENT, SHAKING DEVICE AND METHOD FOR IRRADIATING A MEDIUM IN A BIOREACTOR

(75) Inventors: Marcel Roell, Maur (CH); Lars Boettcher, Melsungen (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 0 days.

(21) Appl. No.: 13/635,769

(22) PCT Filed: Apr. 21, 2011

(86) PCT No.: PCT/EP2011/002044
§ 371 (c)(1),
(2), (4) Date: Sep. 18, 2012

(87) PCT Pub. No.: WO2011/134629
PCT Pub. Date: Nov. 3, 2011

(65) Prior Publication Data
US 2013/0040372 A1 Feb. 14, 2013

(30) Foreign Application Priority Data
Apr. 28, 2010 (DE) .................. 10 2010 018 678

(51) Int. Cl.
*C12M 1/00* (2006.01)
*C12M 1/12* (2006.01)
*C12M 3/06* (2006.01)

(52) U.S. Cl.
CPC ............ *C12M 31/02* (2013.01); *C12M 21/02* (2013.01); *C12M 23/04* (2013.01); *C12M 23/26* (2013.01); *C12M 23/28* (2013.01); *C12M 27/16* (2013.01)

(58) Field of Classification Search
CPC ...... C12M 21/02; C12M 23/04; C12M 23/26; C12M 23/28; C12M 27/16; C12M 31/02; G09F 13/00; G09F 13/04
See application file for complete search history.

(56) References Cited

U.S. PATENT DOCUMENTS 6,287,852 B1 9/2001 Kondo et al.
2005/0254055 A1* 11/2005 Peng ........................... 356/432
(Continued)

FOREIGN PATENT DOCUMENTS

CA 2 341 894 3/2000
CA 2 341 896 3/2000
(Continued)

OTHER PUBLICATIONS

Mikola et al., Bioprocess and Biosystems Engineering, vol. 30, p. 231-241, 2007.*
Translation of International Preliminary Report.

*Primary Examiner* — Michael L Hobbs
(74) *Attorney, Agent, or Firm* — Gerald E. Hespos; Michael J. Porco; Matthew T. Hespos

(57) ABSTRACT

A bioreactor arrangement has a bioreactor and an illuminating body for illuminating a medium in a reactor interior. The illuminating body has at least one emission surface via which light, reflected by at least one end surface into the reactor interior, is emitted. The bioreactor is formed as a container having a transparent wall. The illuminating body is outside the reactor interior, next to at least one subregion of the transparent wall. The illuminating body forms a support surface for the bioreactor with its emission surface. A shaking device has a reactor holder that can be in oscillated, for a bioreactor with a transparent wall. The reactor holder has a two-dimensional illuminating body, the emission surface of which forms a support surface for the
(Continued)

bioreactor, via which light can be reflected into the reactor interior of the bioreactor.

11 Claims, 3 Drawing Sheets

(56) References Cited

U.S. PATENT DOCUMENTS

| | | |
|---|---|---|
| 2007/0113474 A1 | 5/2007 | Everett et al. |
| 2008/0274541 A1* | 11/2008 | Selker ................. B01F 3/04248 435/289.1 |
| 2009/0047722 A1* | 2/2009 | Wilkerson et al. ........ 435/173.7 |
| 2010/0330663 A1 | 12/2010 | Baumfalk et al. |
| 2012/0034679 A1* | 2/2012 | Falber ................... A01G 33/00 435/257.1 |

FOREIGN PATENT DOCUMENTS

| | | |
|---|---|---|
| CA | 2 362 939 | 8/2000 |
| DE | 44 32 515 | 3/1996 |
| DE | 199 93 519 | 8/1999 |
| DE | 298 19 259 | 12/1999 |
| DE | 199 57 116 | 12/2000 |
| DE | 20 2007 013 405 | 12/2007 |
| DE | 10 2008 028 497 | 1/2009 |
| DE | 10 2008 010 780 | 10/2009 |
| EP | 1 173 542 | 5/2000 |
| WO | 2009/069967 | 6/2009 |
| WO | WO 2009069967 A2 * | 6/2009 |
| WO | 2010/016538 | 2/2010 |

* cited by examiner

BIOREACTOR ARRANGEMENT, SHAKING DEVICE AND METHOD FOR IRRADIATING A MEDIUM IN A BIOREACTOR

BACKGROUND OF THE INVENTION

1. Field of the Invention

The invention relates to a bioreactor arrangement, comprising a bioreactor and an illuminating body for illuminating a medium arranged in a reactor interior, the illuminating body comprising at least one emission surface via which electromagnetic radiation, such as light, reflected by at least one end surface into the reactor interior, is emitted.

2. Description of the Related Art

The invention furthermore relates to a shaking device comprising a holder, which can be set in oscillation, for a bioreactor formed as a container comprising a transparent wall.

The invention furthermore relates to a method for irradiating a medium in a bioreactor, which comprises a transparent wall and is set in shaking motions in a shaking device, with electromagnetic radiation, such as light.

For the cultivation of phototrophic cell cultures in bioreactors, besides the ambient conditions, for example temperature, humidity and $CO_2$ content, the illumination is of crucial importance.

DE 298 19 259 U1 discloses a bioreactor arrangement which comprises a photobioreactor, in the reactor interior of which a cylindrical illuminating body is arranged. From a light source arranged outside the reactor interior, light is reflected into the end surface of the illuminating body via a light guide which passes through the reactor wall and is fanned out annularly in the reactor interior, this light then being emitted laterally via the cylindrical surfaces of the illuminating body. For the lateral emission, the transparent illuminating body comprises inclusions, or particles. In order to enhance the lateral emission, the side surfaces of the illuminating body may furthermore have a roughened surface.

A disadvantage with the known bioreactor arrangement is that the reactor wall has to be interrupted in order to introduce the light guide. This leads to a relatively elaborate and expensive configuration of the bioreactor. Such a bioreactor is furthermore not suitable for being used as a foldable single-use bioreactor in the form of a bag.

Furthermore, WO 2010/016538 A1 discloses a photoreactor arrangement in which the reactor interior likewise contains an illuminating body, via the end surface of which light is reflected in and is emitted via lateral emission surfaces. The light is in this case reflected in via LEDs preceding the end surfaces.

This bioreactor arrangement also has the disadvantages mentioned above.

WO 2009/069967 A2 discloses a photobioreactor formed in the shape of a cuboid or cylinder, in the reactor interior of which flat or cylindrical light-emitting illuminating bodies are arranged. Light from LEDs is coupled into the illuminating bodies. To this end, it is necessary to encapsulate the LEDs together with their circuit boards hermetically.

This bioreactor arrangement also has the disadvantage that it is relatively elaborate and expensive. Also, this bioreactor arrangement is not suitable for the use of flexible single-use bioreactors.

Lastly, illuminating bodies in the form of light-guide plates are also known for example from DE 44 32 515 A1 and DE 10 2008 28 497 A1.

In order to ensure the necessary gasification and the necessary nutrient transfer for the medium contained in the bioreactor, or the cell culture, mixers or stirrers are used in the bioreactors.

Particularly in the case of bioreactors which are used as flexible single-use containers, shaking devices are used for mixing which shake the bioreactor with the medium contained, or set it in vibrating or tilting motion.

For instance, EP 1 173 542 B1 discloses a shaking device which comprises a reactor holder for a flexible container, which can be set in oscillation.

A disadvantage with this device, which has essentially been found, is that it cannot be used in conjunction with plant cell cultures, which require defined illumination, as a medium in photobioreactors. The climatic system in the reactor interior should not in this case be interfered with by input of heat, for example heat generated by a light source.

It is therefore an object of the present invention to provide a bioreactor arrangement comprising a bioreactor, which is suitable for being used as a photoreactor for the irradiation of a medium with electromagnetic radiation, in particular light.

It is a further object of the invention to provide a shaking device for a photoreactor formed, in particular, as a flexible container.

It is a further object of the invention to provide a method for the irradiation of a medium in a bioreactor comprising a transparent wall, wherein the bioreactor can be mixed in a shaking device.

SUMMARY OF THE INVENTION

The object relating to the bioreactor arrangement is achieved, in that the bioreactor is formed as a container having a transparent wall, in that the illuminating body is arranged outside the reactor interior, next to at least one subregion of the transparent wall, and in that the illuminating body forms a bearing or support surface for the bioreactor with its emission surface.

Arranging the illuminating body outside the reactor interior makes it possible to configure the bioreactor as a flexible container having a transparent wall. It is thereby also possible for the flexible container, or bioreactor, to be delivered folded and sterilely packed. By forming the emission surface of the illuminating body as a bearing or support surface for the bioreactor, the bioreactor can be simply placed on the illuminating body and, with its wall making contact with the emission surface, necessarily has a defined illumination position with respect to the illuminating body. By shining or reflecting electromagnetic radiation, having the wavelengths necessary for the reaction, in particular light, into the end surface of the illuminating body, virtually no heat input into the reactor interior takes place.

In a preferred embodiment, the illuminating body comprises openings for passing sensors, connections or stirrers through to the bioreactor.

According to a preferred embodiment of the invention, the illuminating body is arranged on a reactor holder of a shaking device. By the arrangement of the illuminating body on the reactor holder of the shaking device, its emission surface forms the bearing or support surface of the reactor holder of the shaking device. It is therefore relatively straightforward for a shaking device known per se now to be used for a bioreactor, formed as a container which for example has flexible walls, which owing to the illuminating body becomes a photobioreactor.

According to another preferred embodiment of the invention, the bioreactor is formed as a flexible plastic bag for single use. By arranging the illuminating body outside the bioreactor, the bioreactor can be formed, or used, as an economical flexible plastic bag for single use.

According to another preferred embodiment of the invention, the illuminating body is formed as a flat plate, a lighting strip comprising a multiplicity of luminous bodies emitting defined wavelengths, in particular LED light sources, being arranged on at least one end surface for reflecting in electromagnetic radiation, in particular light. Owing to the configuration as a flat plate, the illuminating body can be produced relatively easily and economically. In principle, however, it is also possible to adapt the illuminating body to the shape of the bioreactor. It is also possible, for example, to configure the bioreactor cylindrically or in the form of a cup, so that the wall of the bioreactor is supported by the illuminating body. This makes it possible, in particular, to configure the bioreactor cylindrically instead of in the shape of a cushion. Owing to the use of a multiplicity of LED light sources, furthermore, an only a minor, negligible heat development of the light sources takes place outside the reactor interior.

According to another preferred embodiment of the invention, the illuminating body comprises light-scattering particles inside it. The effect of the light-scattering particles is that the otherwise usual total reflection in the illuminating body is interrupted and light reflected in via the end sides emerges laterally from the emission surface. The surface facing away from the bioreactor may in this case be mirrored in order to prevent light from exiting on this side. It is also possible to provide the emission surface with a light-scattering structure. The light-scattering structure may, for example, consist of a roughened surface.

The object relating to the shaking device is achieved, in that the reactor holder comprises a two-dimensional illuminating body, the emission surface of which forms a bearing or support surface for the bioreactor to be received, via which electromagnetic radiation, such as light, can be reflected into the reactor interior of the bioreactor.

Owing to the arrangement of a two-dimensional illuminating body in the reactor holder for the bioreactor, it is readily possible to reflect electromagnetic radiation, in particular light, into the reactor interior of the bioreactor, so that the bioreactor can be used as a photoreactor during the shaking process.

According to a preferred embodiment of the invention, electromagnetic radiation, such as light, which can be reflected in via at least one end surface, is emitted into the bioreactor via the emission surface. The reflection into the bioreactor in this case takes place virtually heat-free, so that the thermal climate of the reactor interior is not affected. By reflection in via the end surface or end surfaces of the illuminating body, the heat developed by the light sources is substantially released to the environment of the bioreactor.

The object relating to the method is achieved, in that the bioreactor is placed in a reactor holder of the shaking device in such a way that at least a part of its wall bears on a bearing or support surface of the reactor holder, which is formed by an emission surface of a two-dimensional illuminating body, and in that electromagnetic rays, such as light, which shines via the emission surface and the wall of the bioreactor into the medium arranged in the reactor interior, is reflected into at least one end side of the illuminating body.

Owing to the fact that luminous bodies are used, which deliver electromagnetic radiation of defined wavelengths, a wide use of the method by the user is possible. The wavelength and the intensity of the radiation may be regulated as a function of the cultivation task. In this case, regulation of the light intensity by means of detection of the biomass formation has proven particularly useful.

The method according to the invention makes it possible in a simple and economical way to shine light into a medium comprising phototropic microorganisms or algae of a photoreactor, mixing of the medium simultaneously being made possible in a shaking device.

Further details of the invention may be found in the following detailed description and the appended drawings, in which preferred embodiments of the invention are illustrated by way of example.

DETAILED DESCRIPTION OF THE PREFERRED EMBODIMENTS

A bioreactor arrangement 1 consists essentially of a bioreactor 2, an illuminating body 3 and a shaking device 4.

Figure 1:
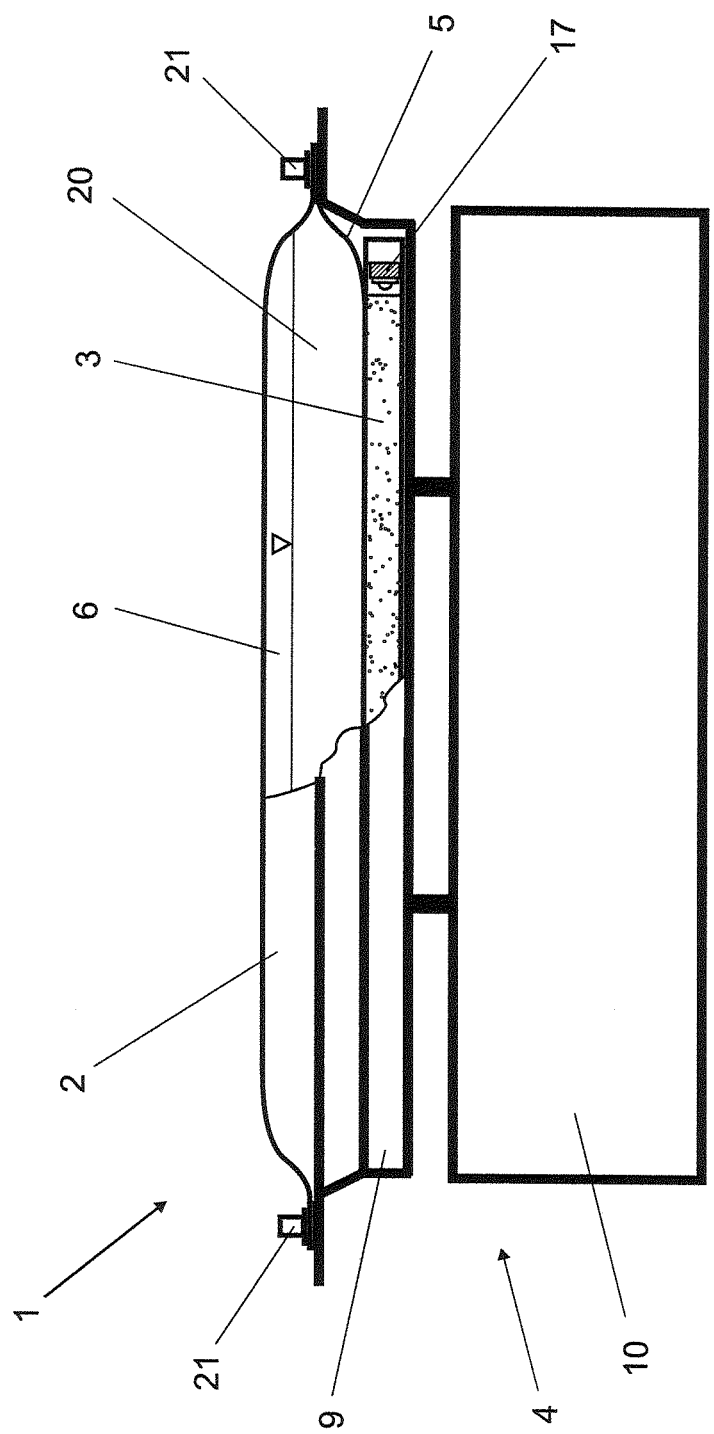
FIG. 1 shows a side view of a bioreactor arrangement, partially in section, with a shaking device.
Figure 2:
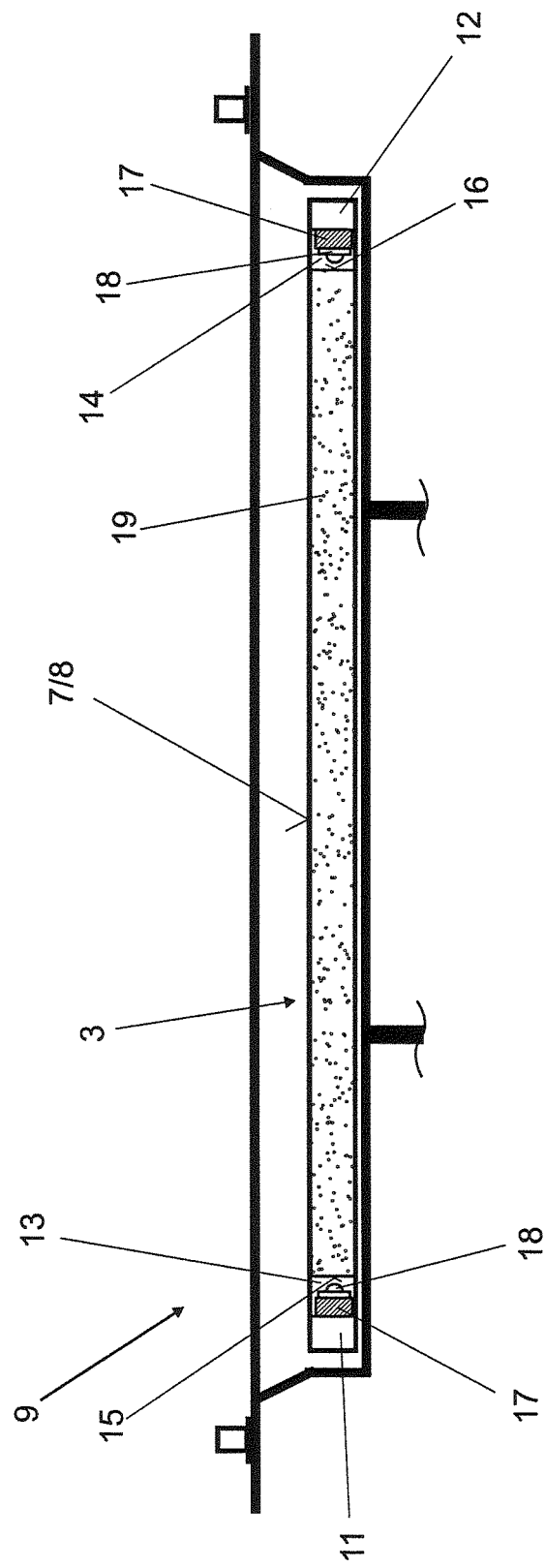
FIG. 2 shows a side view of the reactor holder of the shaking device of FIG. 1 without the bioreactor in an enlarged representation.
Figure 3:
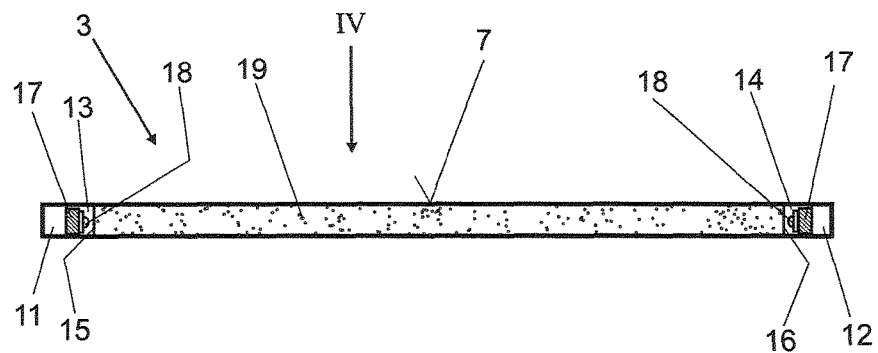
FIG. 3 shows a side view of the illuminating body of FIG. 1 in section.
Figure 4:
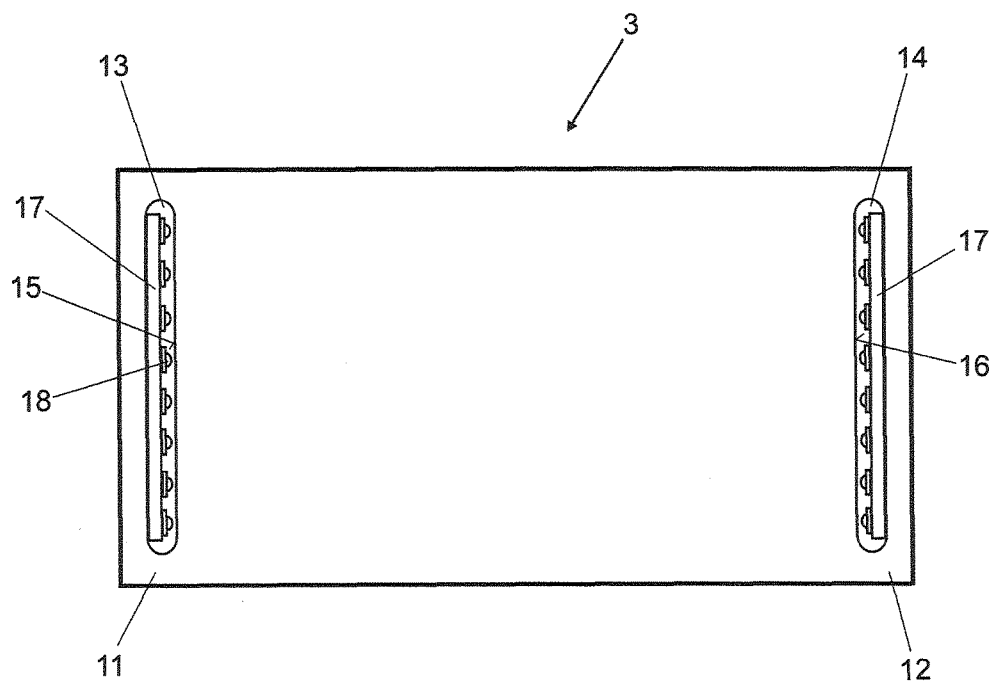
FIG. 4 shows a plan view of the illuminating body of FIG. 3 from the direction IV.

According to the exemplary embodiment of FIG. 1, the bioreactor 2 is configured as a flexible container in the form of a bag with a transparent wall 5, which encloses a reactor interior 6.

Feeds and discharges to and from the reactor interior 6, which are known to the person skilled in the art, have not been represented for better clarity.

With its emission surface 7 facing toward the bioreactor 2, the illuminating body 3 forms a bearing surface 8 of a reactor holder 9 of the shaking device 4. The shaking device 4 comprises a drive and control unit 10, which sets the reactor holder 9 in shaking motion, or oscillation.

According to FIGS. 1 to 4, the illuminating body 3 is formed as a flat plate. On its extreme ends 11, 12, the illuminating body 3 comprises two transversely extending openings 13, 14 which expose the functional end surfaces 15, 16, via which light is reflected into the illuminating body 3. A lighting strip 17 comprising LED light sources 18 is respectively fitted into the openings 13, 14. The light from the LED light sources 18 is reflected in via the end surfaces 15, 16 of the illuminating body 3 and emitted via the emission surface 7 facing toward the bioreactor 2. On its inside, the illuminating body 3 comprises light-scattering particles 19 which are intended to enhance the lateral emission via the emission surface 7. In addition, the emission surface 7 may comprise a light-scattering structure, for example in the form of a roughened surface.

In the exemplary embodiment, the illuminating body 3 is formed from an acrylic glass. In general, the illuminating body 3 may be formed from any desired light-emitting material, including for example glass.

The light emitted via the emission surface 7 is shone through the transparent wall 5 of the bioreactor 2 into the medium 20, lying in the reactor interior 6, which contains the cell culture.

The bioreactor 2 in the form of a bag, which contains the medium 20, is fitted into the reactor holder 9 of the shaking device 4 in such a way that the part of its transparent wall 5 which faces toward the emission surface 7 of the illuminating body 3 bears on the emission surface 7, which forms the bearing surface 8 of the reactor holder 9. The light from the lighting strips 17 with their LED light sources 18 which is reflected into the end surfaces 15, 16 of the illuminating body 3 is reflected and emitted via the emission surface 7, so that it shines through the wall 5 into the medium 20. At the same time, the bioreactor 2 for the reactor holder 9 is set in reciprocating oscillation. The bioreactor 2 may be fixed on the reactor holder 9 by using fastening means 21.

The invention claimed is:

1. A bioreactor arrangement (1), comprising a bioreactor container (2) with a reactor interior (6) for containing a medium (20) arranged in the reactor interior (6), the bioreactor container (2) having a transparent wall (5), an illuminating body (3) arranged outside the reactor interior (6) and having an emission surface (7) next to the transparent wall (5), the emission surface (7) of the illuminating body (3) forming a bearing surface (8) that supports the bioreactor container (2) from below and at least one end surface (15, 16) intersecting the bearing surface (8); and at least one light source (17, 18) arranged to project light into the at least one end surface (15, 16) of the illuminating body (3) and directing the light into the illuminating body (3), the illuminating body (3) being configured so that the light projected into the at least one end surface (15, 16) is redirected within the illuminating body (3) and emitted from the emission surface (7), through the transparent wall (5) and into the reactor interior (6) of the reactor container (2) supported on the emission surface (7).

2. The bioreactor arrangement of claim 1, wherein the illuminating body (3) is arranged on a reactor holder (9) of a shaking device (4).

3. The bioreactor arrangement of claim 1, wherein the bioreactor (2) is a flexible plastic bag for single use.

4. The bioreactor arrangement of claim 1, wherein the illuminating body (3) is a flat plate, and that the at least one light source (17, 18) includes a lighting strip (17) comprising a multiplicity of LED light sources (18) arranged on at least one end surface (15, 16).

5. The bioreactor arrangement of claim 1, wherein the illuminating body (3) comprises light-scattering particles (19) inside.

6. The bioreactor arrangement of claim 1, wherein the emission surface (7) facing toward the bioreactor (2) comprises a light-scattering structure.

7. The bioreactor arrangement of claim 1, wherein the illuminating body (3) is formed from an acrylic glass.

8. A bioreactor arrangement (1), comprising: a flexible bioreactor container (2) with a reactor interior (6) for containing a medium (20), the bioreactor container (2) having a transparent wall (5); an illuminating body (3) arranged outside the reactor interior (6) and defining a movable holder of a shaking device (4), the illuminating body (3) having an emission surface (7) next to the transparent wall (5) and at least one end surface (15, 16) intersecting the bearing surface (8), the emission surface (7) of the illuminating body (3) forming a bearing surface (8) that supports the bioreactor container (2) from below; and a lighting strip (17) comprising a multiplicity of LED light sources (18) arranged on the at least one end surface (15, 16) of the illuminating body (3), the LED light sources (18) directing light into the at least one end surface (15, 16) of the illuminating body (3), wherein the illuminating body (3) is configured so that the light entering the at least one end surface (15, 16) is redirected within the illuminating body (3) from the at least one end surface (15, 16) to the emission surface (7), through the transparent wall (5) and into the reactor interior (6) of the flexible reactor container (2) that is supported on the emission surface (7).

9. The bioreactor arrangement (1) of claim 8, wherein the flexible bioreactor container (2) has no light sources in the reactor interior (6).

10. The bioreactor arrangement of claim 9, wherein the illuminating body (3) comprises light-scattering particles (19) inside.

11. The bioreactor arrangement of claim 9, wherein the emission surface (7) facing toward the bioreactor (2) comprises a light-scattering structure.

* * * * *